US00PP34360P2

(12) United States Plant Patent
Trees

(10) Patent No.: US PP34,360 P2
(45) Date of Patent: Jun. 21, 2022

(54) ***VERBENA* PLANT NAMED 'HOMESTEAD HOT PINK'**

(50) Latin Name: ***Verbena* hybrid**
Varietal Denomination: Homestead Hot Pink

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 113 days.

(21) Appl. No.: 17/400,263

(22) Filed: Aug. 12, 2021

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./263.1, 308
See application file for complete search history.

*Primary Examiner* — Karen M Redden
(74) *Attorney, Agent, or Firm* — Audrey Charles

(57) ABSTRACT

A new and distinct cultivar of *Verbena* plant named 'Homestead Hot Pink', characterized by its bright reddish-purple colored flowers, dark green-colored foliage, and vigorous, spreading growth habit, is disclosed.

1 Drawing Sheet

Latin name of genus and species of plant claimed: *Verbena* hybrid.
Variety denomination: 'Homestead Hot Pink'.

BACKGROUND OF THE INVENTION

The present invention relates to a new and distinct cultivar of *Verbena* plant botanically known as *Verbena* hybrid and hereinafter referred to by the cultivar name 'Homestead Hot Pink'.

The new cultivar originated in a controlled breeding program in Guadalupe, Calif. during July 2013. The objective of the breeding program was the development of *Verbena* cultivars that have abundant flowers, a vigorous spreading growth habit, and powdery mildew resistance.

The new *Verbena* cultivar is the result of cross-pollination. The female (seed) parent of the new cultivar is the proprietary *Verbena canadensis* breeding selection coded 1782-A, not patented, characterized by its medium pink-colored flowers, medium green-colored foliage, and moderately vigorous, spreading growth habit. The male (pollen) parent of the new cultivar is the proprietary *Verbena* hybrid breeding selection coded 13817, not patented, characterized by its dark scarlet-red colored flowers, medium green-colored foliage, and moderately vigorous, mounded growth habit. The new cultivar was selected as a single flowering plant within the progeny of the above stated cross-pollination during August 2014 in a controlled environment in Guadalupe, Calif.

Asexual reproduction of the new cultivar by terminal stem cuttings since August 2014 in Guadalupe, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Homestead Hot Pink' as a new and distinct cultivar of *Verbena* plant:

1. Bright reddish-purple colored flowers;
2. Dark green-colored foliage; and
3. Vigorous, spreading growth habit.

Plants of the new cultivar differ from plants of the female and male parents primarily in having bright reddish-purple colored flowers and a more vigorous spreading growth habit.

Of the many commercially available *Verbena* cultivars, the most similar in comparison to the new cultivar is 'Homestead Purple', not patented. However, in side-by-side comparisons, plants of the new cultivar differ from plants of 'Homestead Purple' in at least the following characteristics:

1. Plants of the new cultivar have more inflorescences per plant under high temperatures than plants of 'Homestead Purple'; and
2. Plants of the new cultivar have bright reddish-purple colored inflorescences different from the purple-colored inflorescences of plants of 'Homestead Purple'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Homestead Hot Pink'. The plants were approximately 16 weeks old. The plants were grown three plants per pot in three-quart containers for approximately 8 weeks in an outdoor nursery in West Chicago, Ill. Plants were given two pinches prior to transplant and one pinch one week after transplant.

DETAILED BOTANICAL DESCRIPTION

Figure 1:
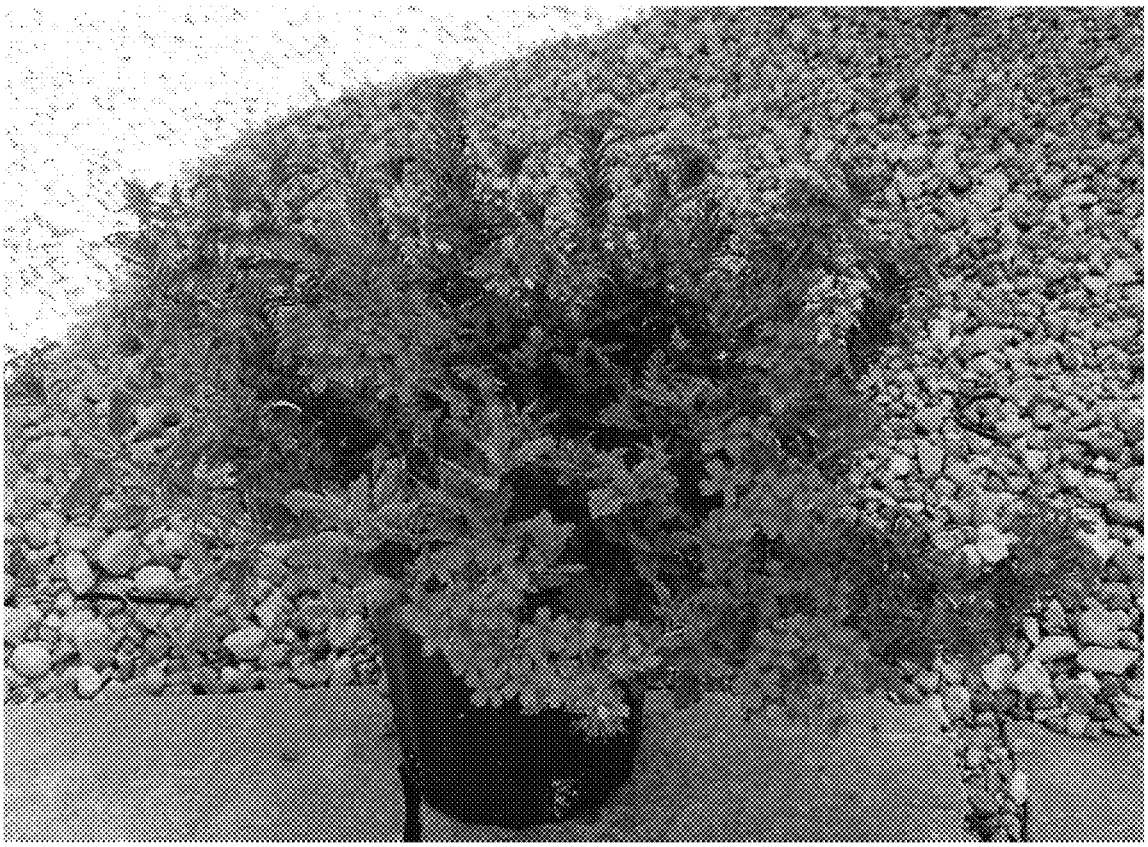
FIG. 1 illustrates a side view of the overall growth and flowering habit of 'Homestead Hot Pink'.
Figure 2:
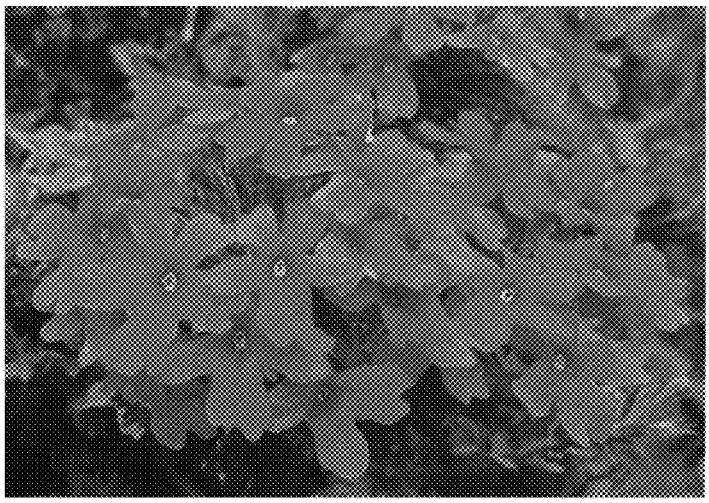
FIG. 2 illustrates a close-up view of an individual inflorescence of 'Homestead Hot Pink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2021 under natural light conditions in Naperville, Ill.

The following descriptions and measurements describe approximately 16-week old plants produced from cuttings from stock plants and grown under conditions comparable to those used in commercial practice. The plants were grown three plants per pot in three-quart containers for approximately 8 weeks in an outdoor nursery in West Chicago, Ill. Plants were given two pinches prior to transplant and one pinch one week after transplant. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Verbena* hybrid 'Homestead Hot Pink'.

Parentage:

*Female parent.*—Proprietary *Verbena canadensis* breeding selection coded 1782-A, not patented.

*Male parent.*—Proprietary *Verbena* hybrid breeding selection coded 13817, not patented.

Propagation:

*Type cutting.*—Terminal stem.

*Time to initiate roots.*—Approximately 7 days.

*Time to produce a rooted cutting.*—Approximately 35 to 42 days.

*Root description.*—Fibrous.

*Rooting habit.*—Freely branching.

Plant description:

*Commercial crop time.*—Approximately 4 to 6 weeks from a rooted cutting to finish in a 10 cm pot.

*Growth habit and general appearance.*—Vigorous, spreading.

*Hardiness.*—USDA Zone 6b (−5° F. to −0° F./−20.6° C. to −17.8° C.).

*Size.*—Height from soil level to top of plant plane: Approximately 16.0 cm. Width: Approximately 36.0 cm.

*Branching habit.*—Freely branching, pinching enhances basal branching. Quantity of main branches per plant: Approximately 9.

*Branch.*—Shape: Square in cross section. Strength: Strong. Length: Approximately 17.0 cm. Diameter: Approximately 3.0 mm. Length of central internode: Approximately 2.0 cm. Texture: Moderately pubescent. Color of young stems: 146C. Color of mature stems: 146B.

Foliage description:

*General description.*—Quantity of leaves per main branch: Approximately 16. Fragrance: None detected. Form: Simple. Arrangement: Opposite.

*Leaves.*—Aspect: Acute to perpendicular to stem, obtuse angle with age. Shape: Ovate to oblong. Margin: Crenate. Apex: Broadly acute. Base: Broadly attenuate to truncate. Venation pattern: Pinnate. Length of mature leaf: Approximately 3.8 cm. Width of mature leaf: Approximately 2.9 cm. Texture of upper and lower surfaces: Moderately pubescent with strigose hairs. Color of upper surface of young foliage: 137A to 137B with venation of 147C. Color of lower surface of young foliage: Closest to 138B with venation of 147C. Color of upper surface of mature foliage: NN137A with venation of 147C. Color of lower surface of mature foliage: Closest to 147B with venation of 147C.

*Petiole.*—Length: Approximately 9.0 mm. Diameter: Approximately 2.0 mm. Texture: Sparsely pubescent. Color: 147C.

Flowering description:

*Flowering habit.*—'Homestead Hot Pink' is freely flowering under outdoor growing conditions from spring through late summer.

*Lastingness of individual flower on the plant.*—Approximately 7 to 9 days.

Inflorescence description:

*General description.*—Type: Corymb. Shape: Hemispherical. Quantity per plant: Approximately 11. Fragrance: None detected. Length or height: 3.2 cm. Width: Approximately 4.5 cm. Quantity of fully open flowers per inflorescence: Approximately 10.

*Peduncle.*—Strength: Strong. Aspect: Erect. Length: Approximately 1.0 cm. Diameter: Approximately 2.0 mm. Texture: Densely pubescent with a mixture of glandular and nonglandular hairs. Gland color: Mixture of N92C and colorless, transparent. Color: 146B.

Flower description:

*General description.*—Type: Sessile, salverform.

*Bud.*—Rate of opening: Generally takes 2 to 3 days for bud to progress from first color to fully open flower. Quantity of unopened inflorescences per plant: Approximately 2.

*Bud just before opening.*—Shape: Elongated, globular at apex. Length: Approximately 1.2 cm. Diameter: Approximately 2.0 mm. Color: Petal portion NN78A, sepal portion 146D with 187A on tips.

*Corolla.*—Shape: Round. Diameter: Approximately 1.7 cm. Depth: Approximately 2.0 cm.

*Petals.*—Quantity: 5, fused at base forming a tube. Shape: Obovate. Appearance: Matte. Margin: Entire. Apex: Emarginate. Length of upper petals from tube: Approximately 8.0 mm. Width of upper petals: Approximately 4.0 mm. Length of lateral petals from tube: Approximately 8.0 mm. Width of lateral petals: Approximately 5.0 mm. Length of lower petal from tube: Approximately 9.0 mm. Width of lower petal: Approximately 6.0 mm. Texture of upper surface: Glabrous with colorless glandular pubescence at base. Texture of lower surface: Sparsely pubescent with a mixture of glandular and nonglandular hairs. Gland color: Mixture of NN78A and colorless, transparent. Color of upper surface when first open: NN78A with deepest color at throat opening. Color of lower surface when first and fully open: NN155D heavily tinted with NN78D. Color of upper surface when fully open: NN78A to NN78B with deepest color at throat opening. Color of whiskers surrounding the opening of the corolla tube: 75B.

*Corolla tube.*—Length: Approximately 1.8 cm. Diameter at proximal end: Approximately 1.0 mm. Diameter at distal end: Approximately 2.0 mm. Texture of outer and inner surfaces: Upper third densely pubescent, lower portion glabrous. Color of outer surface: 155C with an overlay of NN78D at distal end. Color of inner surface: 155C with an underlay of NN78D at distal end.

*Calyx.*—Shape: Tubular with 5 acute tips. Length: Approximately 1.2 cm. Width: Approximately 2.0 mm.

*Sepals.*—Quantity per flower: 5, fused at base. Shape: Linear. Apex: Acute. Length: Approximately 1.2 cm. Width: Approximately 1.0 mm. Texture of inner surface: Glabrous. Texture of outer surface: Densely pubescent with a mixture of glandular and nonglandular hairs. Gland color: Mixture of N92C and colorless, transparent. Color of inner and outer surfaces: 146D with 187A on tips.

*Stipules.*—Shape: Lanceolate. Apex: Acute. Length: Approximately 7.0 mm. Width at base: Approximately 1.0 mm. Texture of inner surface: Glabrous. Texture of outer surface: Densely pubescent with a mixture of glandular and nonglandular hairs. Gland color: Primarily colorless, transparent, rarely with N92C. Color of inner and outer surfaces: 146D with 187A on tips.

*Reproductive organs.*—Androecium: Stamen quantity: 4, didynamous. Stamen length of longer pair: Approximately 2.0 mm. Stamen length of shorter pair: Approximately 1.0 mm. Anther shape: Bilobed, ovoid. Anther length: Approximately 1.0 mm. Anther color: 154C. Pollen amount: None observed. Gynoecium: Pistil quantity: 1 per flower. Pistil length: Approximately 1.7 cm. Stigma shape: Bifid. Stigma length: Less than 1.0 mm. Stigma color: 147C. Style length: Approximately 1.6 cm. Style color: 145D. Ovary diameter: Approximately 1.0 mm. Ovary texture: Glabrous. Ovary color: 144A.

Seed and fruit production: Neither seed nor fruit production has been observed.

Disease and pest resistance: Resistance to powdery mildew common to *Verbena* has been observed.

What is claimed is:

1. A new and distinct cultivar of *Verbena* plant named 'Homestead Hot Pink', substantially as herein illustrated and described.

* * * * *